United States Patent [19]

McKenna et al.

[11] Patent Number: 4,556,743
[45] Date of Patent: Dec. 3, 1985

[54] SELECTIVE DECARBONYLATION PROCESS

[75] Inventors: James E. McKenna, Millburn; Thomas Plocek, Warren, both of N.J.

[73] Assignee: Chem-Fleur International, Inc., Newark, N.J.

[21] Appl. No.: 626,548

[22] Filed: Jul. 2, 1984

[51] Int. Cl.$^4$ .................. C07C 45/78; C07C 45/61
[52] U.S. Cl. ........................... 568/433; 568/438; 585/409
[58] Field of Search .............. 568/433, 434, 438; 585/409

[56] References Cited

U.S. PATENT DOCUMENTS

| | | | |
|---|---|---|---|
| 4,136,122 | 1/1979 | Cotter | 568/438 |
| 4,285,777 | 8/1981 | Jongsma | 568/438 |
| 4,379,026 | 4/1983 | Jongsma | 568/438 |

FOREIGN PATENT DOCUMENTS 1302393  1/1973  United Kingdom ............... 568/434

OTHER PUBLICATIONS

Newman et al., "J. Amer. Chem. Soc.", vol. 65, pp. 1097–1101 (1943).
Hawthorne et al., "J. Org. Chem.", vol. 25, (1960), pp. 2215–2216.
Brown et al., "J. Chem. Soc.", A, pp. 2753–2764 (1970).
Ogata et al., "Chemical Letters", (1972), pp. 487–488.
Ogata et al., "Chemical Abstracts", vol. 75, 140422 (1971).

Primary Examiner—Werren B. Lone
Attorney, Agent, or Firm—Lerner, David, Littenberg, Krumholz & Mentlik

[57] ABSTRACT

A process is disclosed for selectively decarbonylating a compound of the formula

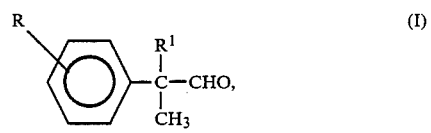

in a mixture containing I and a compound of the formula

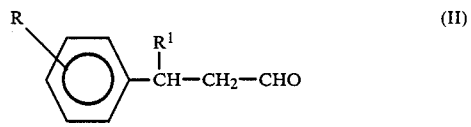

wherein R is hydrogen or at least one lower alkyl group and $R^1$ is hydrogen or a lower alkyl group. In such a process, the mixture is treated with a catalytically effective amount of a palladium catalyst to selectively decarbonylate the compound of formula I therein and the compound of formula II is recovered from the treated mixture.

8 Claims, No Drawings

SELECTIVE DECARBONYLATION PROCESS

BACKGROUND OF THE INVENTION

The present invention relates to a decarbonylation process. More particularly, the invention relates to a selective decarbonylation process employing a palladium catalyst.

Para-t-butyl phenylpropionaldehyde and para-t-butyl-alphamethyl-phenylpropionaldehyde are widely used fragrance materials. Moreover, recently these materials have been suggested for use as fungicides. These compounds are currently prepared from para-t-butyl benzaldehyde or acrolein diacetates. The para-t-butyl benzaldehyde is prepared by a stoichiometric manganese oxidation. This oxidation, however, generates large quantities of solid waste which can present environmental problems. The acrolein diacetates on the other hand are difficult to handle and prepare and such method is a relatively inefficient and expensive one.

Aldehydes can be prepared by various techniques, for example, by hydroformylation. However, aldehydes produced by such method normally appear as mixtures of straight chain and branch chain aldehydes. In this connection, it is many times difficult to provide a relatively pure linear aldehyde product if that is desired. Moreover, the question always remains as to what to do with the undesired branched aldehyde by-product. An alternative use for the branched product can be found, it can be converted into some other desired product, or it can be converted into a material which is used then in some other process or is even discarded.

It would be highly desireable to provide a process which facilitates the separation of straight and branched chain aldehydes, especially of para-t-butyl phenylpropionaldehyde and para-t-butyl-alpha methyl-phenylacetaldehyde. Moreover, it would be very advantageous if the process produced a product which has a commercial utility in itself or is usable as a starting material and in the overall process to obtain the desired product.

Various references have disclosed decarbonylation employing palladium as a catalyst. See, for example, Newman et al., "The Catalytic Dehydrogenation Of 2-Substituted—5, 6, 7, 8-Tetrahydronaphthalene Derivitives" *J.A.C.S.*, Vol. 65, pp. 1097–1101 (1943); Newman et al., "A New Method of Introducing The Neopentyl Group" *J. Org. Chem.* Vol. 31, pp. 3860 et seq. (1966); Hawthorne et al., "Decarbonylation Of Aromatic Aldehydes" *J. Org. Chem.*, Vol. 25, pp. 2215–2216 (1960); *Chemical Abstracts*, Vol. 75, Abstract No. 140422 (1971). However, to our knowledge, no one has suggested that such a palladium catalyst could be employed in a selective decarbonylation of branched aldehyde (especially para-t-butyl-phenylpropionaldehyde) from a mixture also containing a linear aldehyde (e.g., para-t-butyl-alphamethyl-phenylacetaldehyde), for example, from the reaction product mixture of a hydroformylation reaction.

SUMMARY OF THE INVENTION

It has now been found that para-t-butyl phenylpropionaldehyde and other similar aldehydes can be provided from a mixture containing such compounds with their corresponding branched alpha methyl-phenylacetaldehydes by a selective decarbonylation. In the process, a mixture is provided containing a compound of the formula

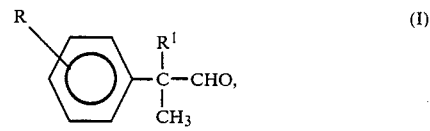

preferably para-t-butyl alpha methyl-phenylacetaldehyde, and a compound of the formula

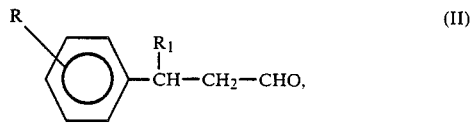

preferably para-t-butyl-phenyl propionaldehyde, wherein R represents hydrogen or at least one lower alkyl group substituted on the phenyl ring and wherein $R^1$ represents hydrogen or a lower alkyl group, preferably methyl. The alkyl groups are preferably of 1 to 6 carbon atoms and can be branched or straight chain. This mixture is treated with a catalytically effective amount of a Pd catalyst to selectively decarbonylate the compound of the formula I therein. The compound of formula II is recovered from the treated mixture.

This process has been found to be highly advantageous in that the palladium catalyzed decarbonylation has been found to be highly selective with regard to the compounds of formula I. Thus, the process provides a relatively simple and economical way for separating a desired phenylpropionaldehyde material from the corresponding branched alpha methyl-phenylacetaldehyde materials, for example, from a hydroformylation reaction product mixture containing both such type compounds. Moreover, the product of the decarbonylation reaction produces a mixture of a compound of the formula

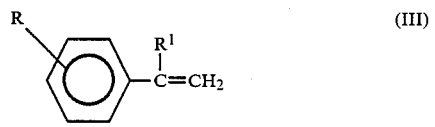

and a compound of the formula

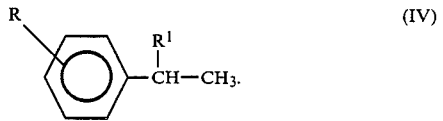

These latter materials can be used as starting materials in a hydroformylation reaction to provide more mixture for the selective decarbonylation process of the invention. In particular, the compound of formula IV can be converted to a compound of formula III, for example, by a dehydrogenation reaction. The compound of formula III can then be used as the starting material in a hydroformylation reaction. Accordingly, the process of the invention provides for economical use of reactants in that the by-products of the selective decarbonylation can be recovered, converted and reused as starting materials for preparing further mixture for the decarbonylation reaction. In addition, the process of the invention is environmentally advantageous in that there is little or no solid waste, in sharp contrast to the other processes for preparing para-t-butyl phenylpropionaldehyde as discussed above.

DETAILED DESCRIPTION OF THE INVENTION

The process of the invention starts with a mixture containing a compound of the formula

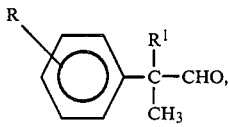

and a compound of the formula

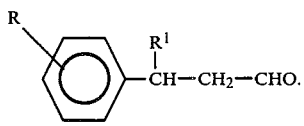

Preferred mixtures include para-t-butyl-phenylpropionaldehyde or phenylpropionaldehyde and its corresponding branched alpha methyl-phenylacetaldehyde. This mixture can be provided by any suitable means. Preferably, the mixture is provided by the reaction product of a hydroformylation reaction in which a compound of the formula

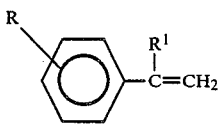

is reacted with hydrogen and carbon monoxide in the presence of an effective amount of a Rh or Co catalyst. This process produces a mixture of the compounds of formulas I and II.

The mixture of the compounds of formulas I and II can be provided neat, i.e., without solvent. However, the mixture of these compounds can be provided in any suitable solvent. An inert solvent which solubulizes the compounds of formulas I and II is preferred. Suitable solvents include ethyl benzene, toluene, xylene, etc.

Palladium has been found to provide a particularly advantageous selective decarbonylation of the compound of the formula I in such mixture. Suitable palladium catalysts for use in the present invention include palladium metal itself, palladium on carbon (powder or granular), and palldium on alumina.

The palladium is provided in the decarbonylation reaction mixture in an amount effective to decarbonylate the compound of formula I under the reaction conditions. Suitable palladium catalyst concentrations for batch reactions are, for example, from about 0.005% to about 0.30%, more preferably from about 0.02% to about 0.08% based on the weight of palladium in the catalyst. For example, if a 5% by weight palladium on carbon catalyst system is employed, the catalyst concentration can suitably range from about 0.1% to about 6.0%.

The decarbonylation process of the invention can also be performed on a continuous basis. In such a continuous reaction, the mixture can be passed through a tubular reactor containing the palladium catalyst, for example, on a fixed bed. In such a continuous reaction, the amount of the palladium catalyst in the continuous reactor varies depending on a large number of factors, including the temperature, pressure, the rate of passage of the reactants through the reactor, etc.

Suitable reaction conditions for performing the decarbonylation process of the invention include temperature ranges of from about 150° C. to about 215° C. or higher. Typically, with higher temperatures more polymeric by-products are obtained, while with lower temperatures a slower rate of reaction is provided. On the other hand, if the reaction is performed continuously, higher temperatures can be employed along with lower residence times to reduce the polymeric by-products.

The decarbonylation reaction can be performed under varying pressure conditions including reduced pressure, ambient pressure, and increased pressures. Typically, the reaction is performed under ambient pressure conditions. However, the use of either a vacuum or a sweep gas such as nitrogen to remove carbon monoxide produced can be employed. In addition, pressures of 30 psi. and above can be employed in the decarbonylation process of the invention.

The decarbonylation process of the invention can be performed in any suitable reactor. For example, it can be simply performed in a flask on the bench scale, in an autoclave, or in a tubular reactor for a continuous process. On a batch scale, the decarbonylation process of the invention typically employs a reaction time of from about 30 minutes to about 12 hours. The reaction time varies depending upon a number of factors, including the temperature employed, the concentration of the palladium, etc.

The decarbonylation process of the present invention is preferably performed under reaction temperature, pressure and catalyst concentration conditions effective such that a high percentage of aldehyde in the decarbonylation reaction product mixture is the compound of formula II. Typically, the decarbonylation process is performed so as to provide a molar ratio of the compound of formula II to the compound of formula I in the decarbonylated reaction product mixture of at least about 4:1, preferably at least about 9:1, and more preferably, at least 20:1.

The mixture of the compounds of formulas I and II are preferably provided as the reaction product of a hydroformylation reaction. Hydroformylation reactions in and of themselves are known in general. In a preferred embodiment of the invention, a compound of the formula

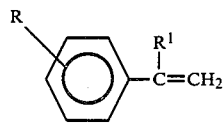

is reacted with hydrogen and carbon monoxide in the presence of a catalytically effective amount of a Rh or Co catalyst, preferably Rh. Such a reaction forms a reaction product mixture containing the compounds of formulas I and II.

Typical temperature conditions for such a hydroformylation reaction range from about 90° C. to about 130°

C. and preferably about 110° C. With higher temperatures, better selectivity towards the straight chain hydroformylation reaction product of the formula II is obtained but there is also more polymeric by-product obtained. Lower temperatures provide more branched product of formula I but less polymeric by-product. Therefore, a temperature balance to obtain a higher ratio of the compound of formula II from the hydroformylation reaction is employed. Other factors also affect this selectivity towards compound of formula II in the hydroformylation, including the ratio of the hydrogen to carbon monoxide employed in the reaction, the use of a ligand such as triphenyl phosphine, and the relative amount of the ligand such as an excess of ligand.

The hydroformylation can be performed employing any suitable hydroformylation catalyst system, e.g., a cobalt or rhodium catalyst system as is conventional in the art. The preferred catalyst system employs a rhodium catalyst. Suitable rhodium catalysts include rhodium metal itself, rhodium on carbon (powder or granular) or a rhodium hydridocarbonyl complex. Ligand materials such as triphenyl phosphine or other suitable phosphine ligand materials are also suitable for use with the rhodium catalyst system employed in the process of the invention. Preferred rhodium catalysts include 5% by weight rhodium on carbon and $Rh(CO)H(TPP)_3$, wherein TPP represents triphenyl phosphine. Such catalyst can be employed with stoichiometric amounts of ligand materials such as TPP or with excess ligand materials in the hydroformylation reaction mixture.

The concentration of the rhodium catalyst in the hydroformylation reaction with the present invention suitably can be from about 0.001% to about 0.2%, more preferably from about 0.01% to about 0.1%, based on the amount of active rhodium in the catalyst. For example, with a 5% by weight rhodium on carbon catalyst, the concentration of the rhodium catalyst in the hydroformylation reaction can range from about 0.02% to about 4.0%.

The hydroformylation reaction can be performed neat employing the reactants as the solvents. This, however provides a greater amount of polymeric by-product. Therefore, it is preferable to employ a solvent in the hydroformylation reaction. Suitable solvents include any solvent which is inert under the reaction conditions and which will solubilize the reactants. Toluene, xylene, etc. are suitable solvents.

The hydroformylation reaction is preferably performed at a pressure of from about 0 to about 50 psi., more preferably from about 0 to about 30 psi., and typically at about 30 psi. This pressure is normally generated via the CO and $H_2$ reactants in the hydroformylation reaction. Preferably, the molar ratio of hydrogen to carbon monoxide in the hydroformylation reaction is from about 4:1 to about 1:4, and typically is 1:1.

As mentioned above, the selectivity of hydroformylation reaction toward the production of a compound of the formula II, i.e., the desired product, is affected by the temperature, pressure, $H_2/CO$ ratio and the solvent system, with the temperature and pressure as the main determinants. Preferably, the reaction conditions are chosen to provide a selectivity ratio (moles of the compound of formula II/moles of the compound of formula I) of 1.5 or greater, preferably 2 or greater.

Again, the reaction time for the hydroformylation reaction depends upon a number of factors including the temperature, rhodium concentration, ligand concentration and excess ligand concentration, etc. Typically, the rhodium-hydroformylation reaction is performed for about one hour to about 24 hours, preferably from about 2 to about 5 hours. The hydroformylation reaction can also be run on a continuous basis employing, for example, a tubular reactor.

The reaction product mixture of the hydroformylation reaction contains a mixture of the compounds of formulas I and II. This reaction product mixture can be employed in the decarbonylation reaction of the invention. However, it is preferred to separate the aldehydes of formulas I and II from most, if not all, of the remainder of the hydroformylation reaction product mixture. Such a separation step can be performed, for example, by distillation of the aldehydes from the reaction product mixture. However, the liquid portion of the reaction product mixture can be separated from the solid catalyst and the residue which collects and this liquid can be treated directly in the decarbonylation process of the invention.

The decarbonylation reaction of the invention can then be performed in the manner described above. Preferably, the desired product, i.e., the compound of formula II, is recovered from the decarbonylation reaction product mixture via, for example, distillation.

The by-products of the decarbonylation reaction are a compound of the formula

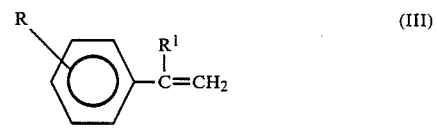

and a compound of the formula

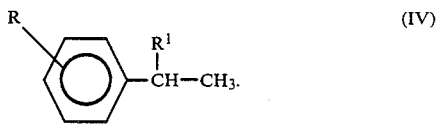

These by-products can advantageously be employed as starting materials for the hydroformylation reaction. Specifically, the compound of formula III is the desired starting material for the hydroformylation reaction. The other by-product, namely the compound of formula IV, can be converted to the desired starting material for the hydroformylation reaction by, for example, dehydrogenation by techniques well known in the art. Other techniques for converting the compound of the formula IV to the compound formula III include oxidation to the phenyl carbinol, followed by dehydration, again by techniques well known in the art.

By employing the by-products of the decarbonylation process of the invention for further use as starting materials in the hydroformylation process, economic use of reactants is achieved and environmental problems avoided. In particular, with the process of the invention employing the hydroformylation reaction followed by the decarbonylation and subsequent conversion of the by-products of the decarbonylation to starting materials for the hydroformylation, relatively small amounts of solid waste are obtained, especially when compared to the high amounts of solid waste obtained by the prior art process employing, for example, manganese oxidation.

The compound of formula II can be reacted via the Mannich reaction to produce other desirable fragrance ingredients of the formula

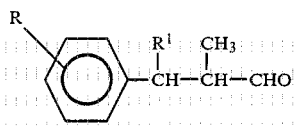

by techniques known in the art for such reaction. A preferred compound of such reaction is

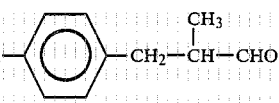

The following examples are intended to illustrate, but not to limit, the present invention:

EXAMPLE 1

A mixture of 175 g. of para-t-butylstyrene, 175 g. of toluene, 40 g. of triphenylphosphine, and 3 g. of 5% rhodium on carbon (powder) were charged to a one-liter autoclave, equipped with a stirrer and heating mantle. The autoclave was purged free of air, and pressurized to 30 psig. with a 50:50 mixture of hydrogen and carbon monoxide. The reaction mixture was heated with stirring to 110° C., maintaining the pressure at 30 psig.

After 12 hours, 16% of the para-t-butylstyrene was unreacted. The products, para-t-butyl-alpha-methyl-phenylacetaldehyde and para-t-butyl phenylpropionaldehyde, were formed in a molar ratio of 34:66.

EXAMPLE 2

The procedure of Example 1 was repeated, except that 0.5 g. of triphenylphosphine and 1.25 g. of rhodium on carbon was used. After 3 hours, 8% of the para-t-butylstyrene was unreacted, and the branched: linear product molar ratio was 37:63.

EXAMPLE 3

The procedure of Example 1 was repeated, using 35 g. of para-t-butylstyrene, 35 g. of toluene, and 0.25 g. of hydridocarbonyltristriphenylphosphine rhodium [Rh(CO)H(TPP)$_3$]. After 2 hours at 100° C., 3% of the para-t-butylstyrene was unreacted, and the branched: linear product molar ratio was 38:62.

EXAMPLE 4

15 g. of the product mixture obtained in Example 1 was charged into a 50 ml. glass round-bottom flask, equipped with a magnetic stirring bar and a reflux condenser. 0.15 g. of 5% by weight palladium on carbon powder was added, and the mixture was heated to 210° C. with stirring. Carbon monoxide was rapidly evolved, and after ½ hour, the branched: linear molar ratio was 3.4:96.6. The branched isomer had selectively decarbonylated primarily to para-t-butyl-ethylbenzene.

EXAMPLE 5

A mixture of 32 g. of phenylpropionaldehyde, 32 g. of alphamethyl-phenylacetaldehyde and 0.6 g. of 5% by weight palladium on carbon powder were charged to a 100 ml. flask, equipped with a magnetic stirring bar and a distillation head. The mixture was heated to 180° C. with stirring, and the ethylbenzene was distilled out of the reaction mixture as it formed. After 3 hours, the branched: linear molar ratio was 3:97.

EXAMPLE 6

The procedure of Example 5 was repeated, using 135 g. of phenylpropionaldehyde, 15 g. of alphamethyl phenylacetaldehyde, and 1.4 g. of the palladium on carbon. After 3 hours, the branched: linear molar ratio was 2:98, and the temperature had dropped to 155° C.

EXAMPLE 7

15 g. of a solution containing 95% by weight of alphamethyl phenylacetaldehyde and 3% by weight of phenylpropionaldehyde was put into a 50 ml. glass flask equipped with a magnetic stirring bar and a reflux condenser. 0.15 g. of 5% by weight palladium on carbon powder was added and the mixture was heated with stirring to 150° C. At the end of four hours, the reaction mixture contained 74% by weight ethyl benzene and styrene, 18% by weight alphamethyl phenylacetaldehyde and 3% phenylpropionaldehyde. This example demonstrates the high selectivity of the decarbonylation towards the alphamethylphenylacetaldehyde since the amount of the alphamethyl phenylacetaldehyde is greatly reduced (converted to ethyl benzene and styrene) while the amount of the phenylpropionaldehyde remains relatively unchanged.

It will be understood that the embodiments described above are merely exemplary and that persons skilled in the art may make many variations and modifications without departing from the spirit and scope of the invention. All such modifications and variations are intended to be included within the scope of the invention as defined by the appended claims.

What is claimed is:

1. A process for selectively decarbonylating a compound of the formula

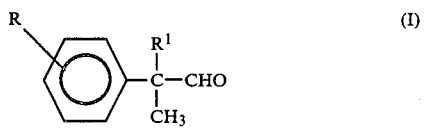

in a mixture containing I and a compound of the formula

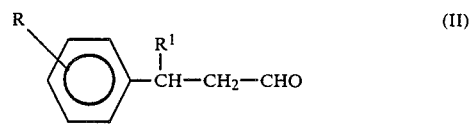

wherein R represents hydrogen or at least one lower alkyl group and R$^1$ represents hydrogen or a lower alkyl group, said process comprising the steps of providing such a mixture; treating the mixture with a catalytically effective amount of a Pd catalyst and at a temperature and pressure effective to selectively decarbonylate the compound of formula I therein; and recovering the compound of formula II from the treated mixture.

2. A process according to claim 1, wherein the mixture is provided by reacting a compound of the formula

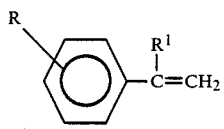

with hydrogen and carbon monoxide in the presence of a catalytically effective amount of Rh or Co catalyst to form a reaction product mixture containing the compounds of formulas I and II.

3. A process according to claim 1, wherein the treating step produces a mixture containing a compound of the formula

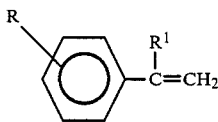

and a compound of the formula

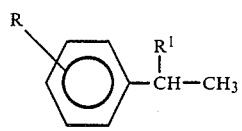

and wherein the compound of formula IV therein is converted to a compound of formula III.

4. A process according to claim 3, wherein the compound of formula IV is converted by dehydrogenation.

5. A process according to claim 2, wherein at least part of the compound of formula III is provided from the decarbonylation of the compound of formula I.

6. A process according to claim 1, wherein R is a para-tertiary butyl group and $R^1$ is hydrogen.

7. A process according to claim 2, wherein the rhodium catalyst is selected from rhodium on carbon and a rhodium hydridocarbonyl complex.

8. A process according to claim 1, wherein the Pd catalyst is Pd on carbon.

* * * * *